United States Patent

Patacsil et al.

[11] Patent Number: 6,132,379
[45] Date of Patent: Oct. 17, 2000

[54] METHOD AND APPARATUS FOR ULTRASOUND GUIDED INTRAVENOUS CANNULATION

[76] Inventors: Estelito G. Patacsil; Amelia V. Patacsil, both of 7740 E. Misty Glen Ct., Anaheim Hills, Calif. 92808

[21] Appl. No.: 09/185,789

[22] Filed: Nov. 4, 1998

[51] Int. Cl.$^7$ ..................................................... A61B 8/00
[52] U.S. Cl. .......................................................... 600/459
[58] Field of Search ................................... 600/443, 472, 600/455, 461, 116, 493, 300, 459, 437; 73/618

[56] References Cited

U.S. PATENT DOCUMENTS

| | | | |
|---|---|---|---|
| 3,888,238 | 6/1975 | Meindl et al. | 600/455 |
| 5,050,610 | 9/1991 | Oak et al. | 600/437 |
| 5,167,629 | 12/1992 | Vertenstein et al. | 600/116 |
| 5,570,694 | 11/1996 | Rometsch | 600/493 |
| 5,590,658 | 1/1997 | Chiang et al. | 600/447 |
| 5,722,412 | 3/1998 | Pflugrath et al. | 600/459 |
| 5,758,650 | 6/1998 | Miller et al. | 600/461 |
| 5,830,131 | 11/1998 | Caro et al. | 600/300 |

OTHER PUBLICATIONS

Jones et al HandheldDoppler ultrasound medical device with cordless probe Jun. 24, 1997.
Maslak et al Steered Linear Color Doppler Imaging May 14, 1991.
Lederman et al Digital Rectilinear Ultrasonic Imaging system Nov. 28, 1978.

*Primary Examiner*—William E. Kamm
*Assistant Examiner*—Maulin Patel

[57] ABSTRACT

A dual mode handheld ultrasonic device is provided for guiding a venous access catheter into a patient's peripheral vein. It provides B-mode imaging with a predetermined aperture and operating frequency which locates and displays a gray scale cross-sectional image of the target blood vessel. A single doppler beam in a separate mode detects the same blood vessel and creates a single scanline image superimposed to such B-mode cross-sectional image. Simultaneously, the intensity of the positive doppler shift detected by the single doppler beam as it hits the target blood vessel activates a plurality of light emitting diode (LED) indicator lights with varying voltage requirements mounted in the scanhead. Activated LED indicator lights forms an arrow pointing inferiorly perpendicular to the target vessel which guides a physician or a paramedical professional to the precise catheter insertion spot on a patient's extremity while simultaneously viewing the target blood vessel's cross-section on the display screen.

9 Claims, 8 Drawing Sheets

METHOD AND APPARATUS FOR ULTRASOUND GUIDED INTRAVENOUS CANNULATION

BACKGROUND—FIELD OF INVENTION

The present invention relates to the use of ultrasound guidance for locating and cannulating peripheral blood vessels which can be performed by both medical and paramedical professionals such as registered nurses, licensed vocational nurses, paramedics, laboratory phlebotomists, researchers, portamedics and emergency room and critical care staff etc.

Intravenous cannulation is an invasive procedure wherein an intravenous catheter is blindly inserted into the lumen of a peripheral blood vessel through the patient's skin. The procedure is performed by the above-mentioned health care providers primarily for drawing blood from patient's arm for diagnostic purposes or for administration of medications and intravenous fluids to treat or save a patient's life. Successful cannulation is highly dependent on the dilatation of the target blood vessel caused by tourniquet application above the level of the insertion site. The dilatation displaces the overlying skin superiorly which subsequently becomes evident to the clinician as an obvious skin bulge on the target site. On a high percentage of patients, especially the seriously ill, geriatric, pediatric and neonatal patients, the obvious bulging of the skin, in reality, rarely happens. Instead, the clinician resorts to multiple attempts that frequently fails. As a result, patient mortality rate is on the rise due to delay of treatments brought about solely or partly by inaccessible intravenous lifelines. This is presently a big problem in health care worldwide which has been addressed but has never been solved.

BACKGROUND—DESCRIPTION OF PRIOR ART

Alternative routes for administration of emergency medications during cardiopulmonary resuscitation other than intravenous route have been demonstrated in practice but only a limited number of medications can be administered. Still, all clinicians prefer to attempt an intravenous access first, for all patients. Alternate routes of administration such as central venous catheter insertion carries big risks or complications that may even jeopardize the patient's life. This special procedure can only be performed by a physician.

The need for a device accurate IV insertion that can be operated by both medical and paramedical professionals such as registered or vocational nurses, paramedics, laboratory phlebotomists, therapists, researchers etc. is critical, without posing serious risks to the patients health. This objective can be achieved by a simplified ultrasound guidance system dedicated to intravenous cannulation that has simple user controls to be able to be operated by the above-mentioned health care providers.

Prior art that utilizes ultrasound imaging is used mainly for medical diagnostics not for dedicated use for intravenous cannulation. Typical ultrasound imaging systems consists of a large rack mounted image processing and image screen and connected by a large cable to a transducer that transmits ultrasonic waves to human tissues being interrogated then receives returning acoustic echoes, converts data to a viewable format by the amplifying, achieving attenuation and focusing the combined signals for dynamic imaging. Conventional ultrasound systems are very complex systems involving a lot of delay and sum circuitry for dynamic focusing. They utilize multiple operating frequencies for different areas of study. Operators of these systems needs formal specialized training and certification from an accredited school and are referred to as sonographers. Only these sonographers can technically operate these complex machines. The large console's use for routine intravenous insertion guidance is high impractical. Typical ultrasound systems involve doppler processors needed for providing two-dimensional depth and Doppler information in color flow images. Rack mounted ultrasound systems needs a lot filters for clutter cancellation and requires millions of operations per second to be implemented and therefore requires hundreds of chips and dissipates hundreds of watts of power. Portable ultrasound system U.S. Pat. No. 5,590,658 January 1997 to Chiang et al., which has similar features as its large console counterparts but offers portability. The pulser and beamforming circuitry and other signal processing functions have been integrated in the scanhead. Although it is smaller in size compared to the rack mounted console, its main purpose and function is for medical diagnostics and was designed to allow use of multiple transducer systems with variable operating frequencies to study various parts of human anatomy like the pelvis, heart etc., and therefore highly impractical for use in routine intravenous cannulation. The complexity of operation in design of the portable system is reserved for registered sonographers only. Another disadvantage is that the chances that the institution or the hospital hiring a registered sonographer for this routine purpose is highly unlikely. Additionally, it is still large enough to be used for daily routine intravenous cannulation. It lacks features especially designed for needle guidance e.g. needle insertion spot LED indicators, a feature that guides the operator to the exact spot where the needle should be inserted and other dedicated features as well, because it was not designed for this purpose.

Another prior art relates to a hand-held ultrasonic diagnostic instrument U.S. Pat. No. 5,722,412 Pflugrath et al Mar. 3, 1998. A fully functional hand-held ultrasonic instrument wherein all transducer elements in curved array configuration and image processing systems are integrated in a single housing. Again, the advantages of the present invention over Pflugrath's handheld diagnostic system are the same as with the portable imaging system described above. It can only be operated by a licensed sonographer and results interpreted by a licensed radiologist. Its main purpose is to diagnose a patient's condition based upon the specific body organ being examined as well as documentation. It was not designed for use in daily routine intravenous cannulation guidance. It lacks features specific to needle guidance as mentioned above. The design, purpose and user controls are too complex for other paramedical professionals to operate.

Several devices where introduced for guiding needles into blood vessels consisting of ultrasound transducer coupled to a backing member with a cylindrically shaped hole for accepting a hypodermic needle. It transmits ultrasonic waves and the reflected energy is doppler shifted in frequency from the transmitted sound wave due to movement of blood cells. The reflected signal is detected and amplified and an audible signal is generated. The intensity of doppler sounds guides the operator to the vessel interest. The disadvantage of this is that relies on the audible signal as guide. There is no real time imaging of the vascular anatomy although it uses ultrasound technology. There is still a great deal of risk of failing to successfully cannulate the target vessel because the needle is being introduced blindly especially to patients who are critically ill and dehydrated, pediatrics and neonates. Other devices includes a hollow needle with a sharpened end for penetrating tissue, a trochar including a transducer mounted for transmitting and receiving ultrasonic waves through the sharpened end of the needle. The operator is guided by the ultrasound transducer mounted on the trochar. Again, this has disadvantages the same as mentioned above. Prior art to mainly utilizes ultrasound for needle guidance by amplifying returning signals to an audio monitor and either probe, trochar or needle mounted transducer elements, not by real time imaging of the target blood vessel.

SUMMARY

A principal object of the invention is to provide a dual mode ultrasonic handheld intravenous cannulation guide by implementing a fixed high frequency B-mode imaging system to create a real-time display of a superficial blood vessel's cross-section. In addition a single element doppler scanline utilizing the center element of the array superimposed to the B-mode grayscale image. The doppler scanline will serve as a marker that is viewed by the operator and will be the target area for cannulation. The entire imaging system includes an array of piezoelectric elements arranged in a linear configuration enclosed in a small scanhead that can be easily manipulated by hand. This handheld coupled to the main housing by a coiled cable for retractability during frequent use. The main housing consists of a common handheld enclosure with one or more separate enclosures for the power system and main microprocessor area. Complex circuitry packaging in a handheld housing was possible by integrating a lot all functions in small integrated circuits like the pulse generator, beamforming functions, scanned conversion etc. Additionally, the system only requires a small transducer aperture, therefore, fewer elements are needed to perform its function, hence, fewer transmit and receive channels are implemented.

Simultaneously, the received doppler frequency is converted into an electrical voltage which illuminates a plurality of light emitting diode (LED) indicator lights with varying voltage requirements mounted in the scanhead and forms a vertical configuration similar to a downward arrow pointing and guiding the operator to the precise spot of needle insertion with respect to the imaged and sensed location of the target blood vessel.

The entire intravenous insertion guidance system is simple to operate with minimal basic user controls and is intended to be operated by both medical and paramedical professionals routinely performing intravenous cannulation.

OBJECTS AND ADVANTAGES

Accordingly, several objects and advantages of the present invention from prior art are described below:

1. To provide a dual mode handheld ultrasound imaging device dedicated for intravenous cannulation guidance that can be easily carried by an operator from patient to another patient.
2. It provides the grayscale cross-sectional B-mode imaging of the target vessels which allows the operator to visualize the target blood vessel he or she is working on for a far more accuracy than just the merely relying on doppler acoustic intensity as guide.
3. It uses B-mode imaging with a single scan line Doppler vessels sensor which can possibly be used for other bedside functions beyond the appended claims.
4. It provides a simplified cross-sectional imaging, which allows visualization of the venous lumen to immediately assess the needle placement by manually steering that scanhead for a longitudinal view of the cannulated vessel.
5. It provides a visible marker of the target vessel on the display by creating a single Doppler scanline as it traverses such target blood vessel.
6. To provide means for illuminating markers (LED indicator lights) mounted on the scanhead housing to guide the operator to the exact spot of needle insertion and to guide such needle into the venous lumen in real time.
7. It provides an ultrasound device with fewer and simple user controls for intravenous cannulation that can be operated by both medical and paramedical professionals such as registered and vocational nurses, paramedics, IV therapists, clinical laboratory phlebotomists, researchers, i.e. IV certified emergency room staff for fast and accurate intravenous access.
8. The invention does not require any specialized needles or syringes for cannulation. It allows use of any regular intravenous access catheters in any form, by any manufacturer, currently be used worldwide.
9. To provide intravenous access guide that reduces patient trauma secondary to multiple cannulation attempts.
10. To provide intravenous access guide that can dramatically decrease time delay of establishing IV lifeline in critical situations by paramedics in the field which can save lives.
11. To provide intravenous access guide that will reduce the delays in administration of blood and blood products secondary to unsuccessful intravenous insertion attempts.
12. To provide an intravenous access guide that reduces delays in establishing intravenous lifelines in the intensive care units and in the regular hospital areas for administration of intravenous fluids and critical care medications.
13. To provide the intravenous access guide that reduces delays in establishing intravenous lifelines in cardiorespiratory arrest situations in the emergency room in other areas of the hospital that can directly save a patient's life.
14. To provide intravenous access guide that can dramatically reduce hospital costs of equipment for alternative access routes and physician's professional fees for insertion of central venous access secondary to failed intravenous cannulation attempts
15. To provide intravenous access guide to quickly assess placement status of newly established intravenous line.
16. To provide intravenous access guide that can be used for early recognition of intravenous infiltration to avoid patient complications.
17. To provide intravenous access guide that can quickly establish an intravenous site to doing mass blood donation.

Still further objects and advantages will become apparent from a consideration of the ensuing description and accompanying drawings.

Figure 1:
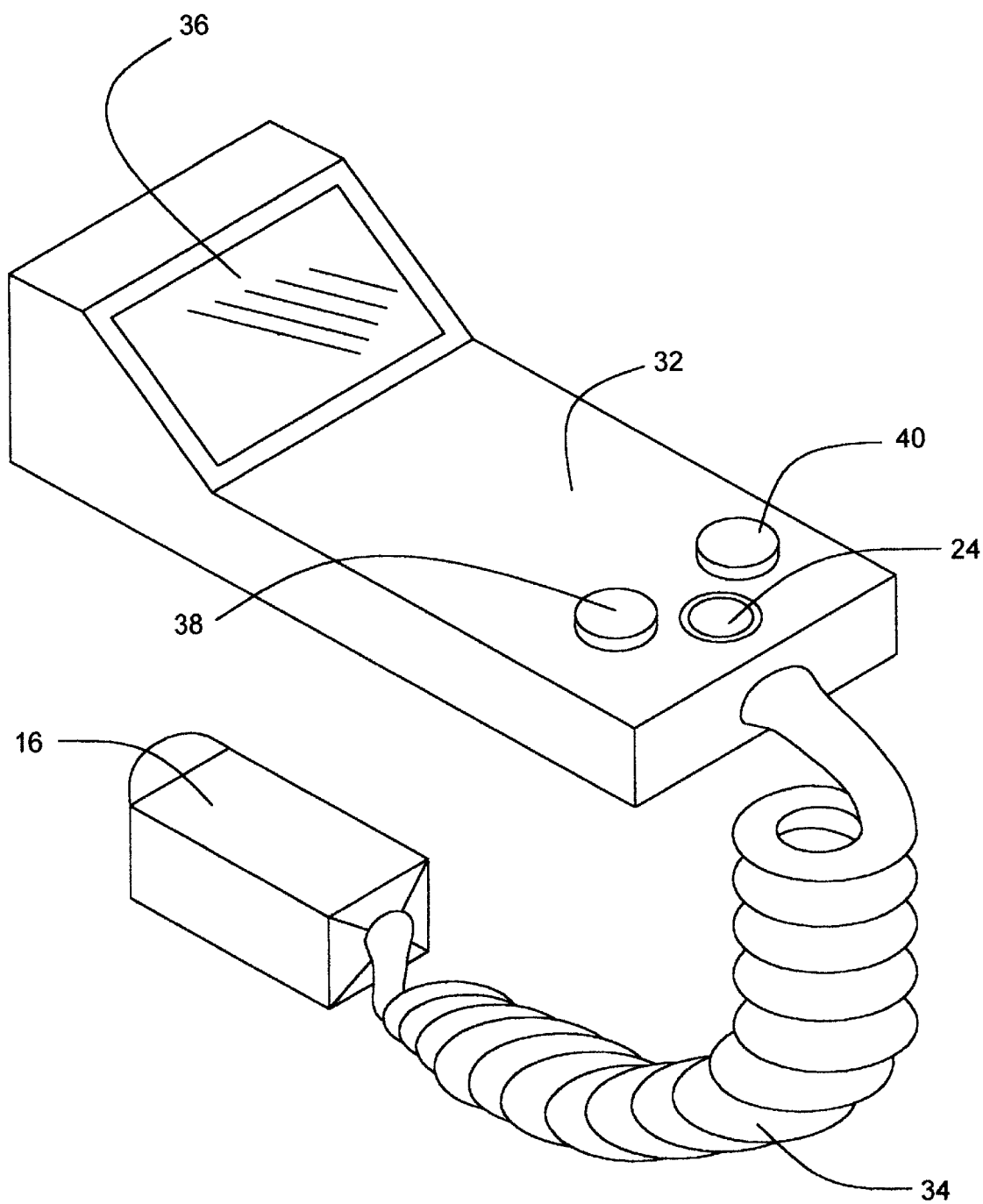
FIG. 1 is a schematic pictorial view all of a preferred embodiment of the invention.

REFERENCE NUMERALS 10 pulse generator
12 multiplexers
14 array (a–n)
16 scanhead
18 target blood vessel
20 coupling gel holder
22 coupling gel
24 on/off power switch
26 center element (c)
28 RISC processor
30 program memory
32 main housing
34 coiled cable
36 LCD display
38 gain control knob
40 brightness/contrast adjustment knob
42 rechargeable battery
44 power supply regulator
46 time gain compensation (TGC)
48 beamformer
50 A/D converter
52 scan conversion
54 B-mode frame memory
56 vascular cross-section
58 single doppler scanline
60 high voltage driver
62 doppler receiver
64 demodulator
66 low pass filter
68 doppler shift frequency
70 bandpass filter
72 frequency to voltage converter
74 intravenous needle
76 light emitting diode LED 1–3 indicator lights
78 patient's extremity
80 rubber strap
82 needle pathway
84 rubber strap hook
86 B-mode scan
88 power subsystems
90 grayscale mapping
92 mixer
94 sample & hold
96 blood flow direction

PREFERRED EMBODIMENT—DESCRIPTION

Figure 10:
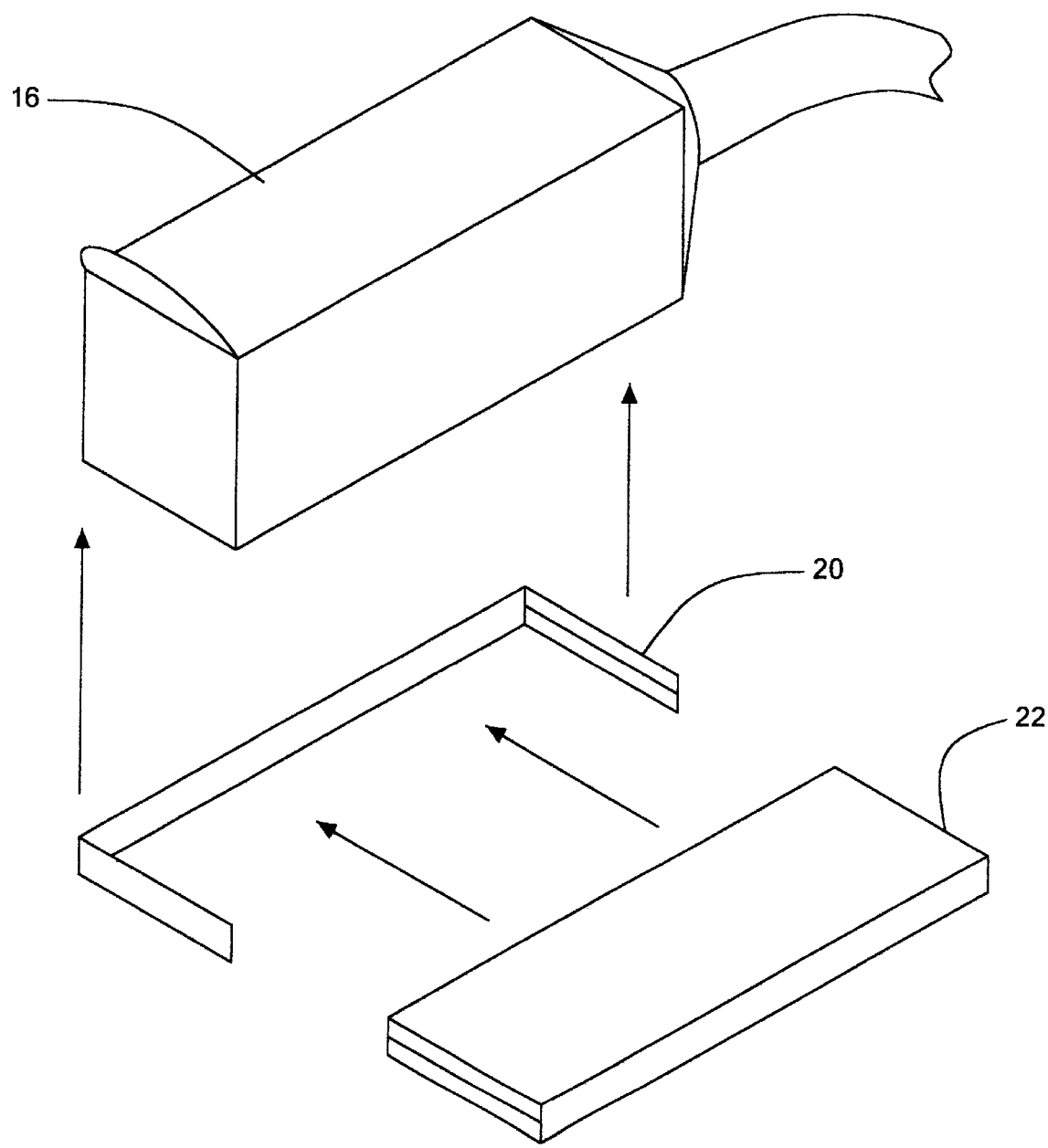
FIG. 10 is an isometric view of the coupling gel cylinder, has preferred embodiment of the invention, and coupling gel contained therein for proper ultrasonic wave propagation to the region of interest. From App program

FIG. 1 is a schematic pictorial view of a preferred embodiment of the invention where it is shown as a dual mode intravenous cannulation guidance system wherein the whole architecture is packaged in a handheld housing coupled to a small transcutaneous scanhead by a coiled cable. Packaging such elaborate circuitry, such as in bulky architecture in prior art designs, to a small housing enclosure is possible and has been demonstrated in the U.S. Pat. Nos. 5,722,412 and 5,590,658. It involves judicious implementation of integrated circuitry wherein main image processing functions are integrated in small chips such as the implementation of application specific IC's or high speed, low power CMOS microchip technology. The preferred embodiment of the invention employs funtional integration on microchips which involves the pulse generator 10, multiplexers 12 integrated with high voltage drivers to drive the transducer elements of the array 14a–14n, where "n" represents the total number of elements. The integrated circuitry is also adapted to be operated cannulate lower voltages than conventional circuitry and, consequently, allowing maintenance of low power dissipation and efficient performance with minimal degradation secondary to thermal effects. This also assures that the patient does not suffer from any potential harmful thermal effects. The preferred embodiment includes a plurality of transducer elements which is of a linear type array configuration mounted in a rectangular enclosure scanhead 16 with a relatively small aperture to locate and cannulate superficial blood vessels 18 in the small area preferably in the general region where the median basilic and median cephalic veins are anatomically superficial. By way of example, a total of 8 or more elements can be employed. The more elements implemented results in improved resolution. These vessels are preferred due to their superficial anatomical location, size and stability. In the preferred embodiment, a flat linear array of transducer piezoelectric elements 14 a–14 n are activated. The transducer scanhead 16 can be manually manipulated or steered by the operator wherein the aperture may be attached to a separate flat holder 20 filled with coupling gel 22 that has a special attachment to the scanhead aperture FIG. 10. This preferred embodiment minimizes the accumulation of coupling gel 22 in the region of interest as a result of manual scanhead 16 manipulation normally done on a conventional imaging procedure. The special coupling gel holder 20 and attachment may prevent a break into sterile technique required to perform a venipuncture procedure. The operator starts the operation by pressing the on/off power switch 24 to "on" to power up and boot the system. The operator then applies and manipulates the scanhead in the region of interest with the coupling gel 22 and the coupling gel holder 20 to improve transmission of ultrasonic acoustic beam. The transducer elements are driven sequentially at a predetermined frequency by the high voltage drivers integrated with the transmit multiplexer 12 controlled by the pulse generator 10. The pulse generator also has a separate predetermined pulse repetition frequency for a separate Doppler processor from the echoes received from the center element 26 C. All operations of the entire imaging system including the pulse generator 10 is controlled by (Reduced Instruction Set Computing) RISC processor 28 through a program memory 30. The sequentially pulsed elements 14a–14n with a preferred operating frequency of 7.5 to 10 Mhz for improved axial resolution, which is ideal for imaging superficial blood vessels especially in pediatric and neonatal patients, in turn propagates a spherical waveform in a direction perpendicular to the transducer elements (90 degrees) to obtain a cross-sectional image of the area of interest. Returning echoes from different lines of sight are picked up or received by the same transducer element at varying intensities. The scanhead 16 is coupled the main housing 32, in a handheld design comprising of one or more enclosures, preferably by a coiled cable 34 for retractability during use but with a predetermined length to minimize signal loss.

The main housing 32 exterior comprises of an LCD display 36 at an angle to be best viewed by the operator. As an alternative embodiment, the display can be flip-top type similar to a laptop computer display so the viewing angle can be changed to reduce glare during outdoor use. The entire imaging system is lightweight and weighs approximately the less than 5 pounds.

Several user controls are employed in the preferred embodiment for simplicity to be easily controlled by the intended users, comprising of a gain control knob 38, brightness/contrast adjustment knob 40 and the on/off power switch 24.

The power to the unit is supplied by a rechargeable battery 42 coupled to 8 power supply regulator to all power subsystems for variable power requirements of the whole imaging system. The power system is well-known to a person skilled in the art, and can be optimized, hence, will not be described in detail.

Figure 2:
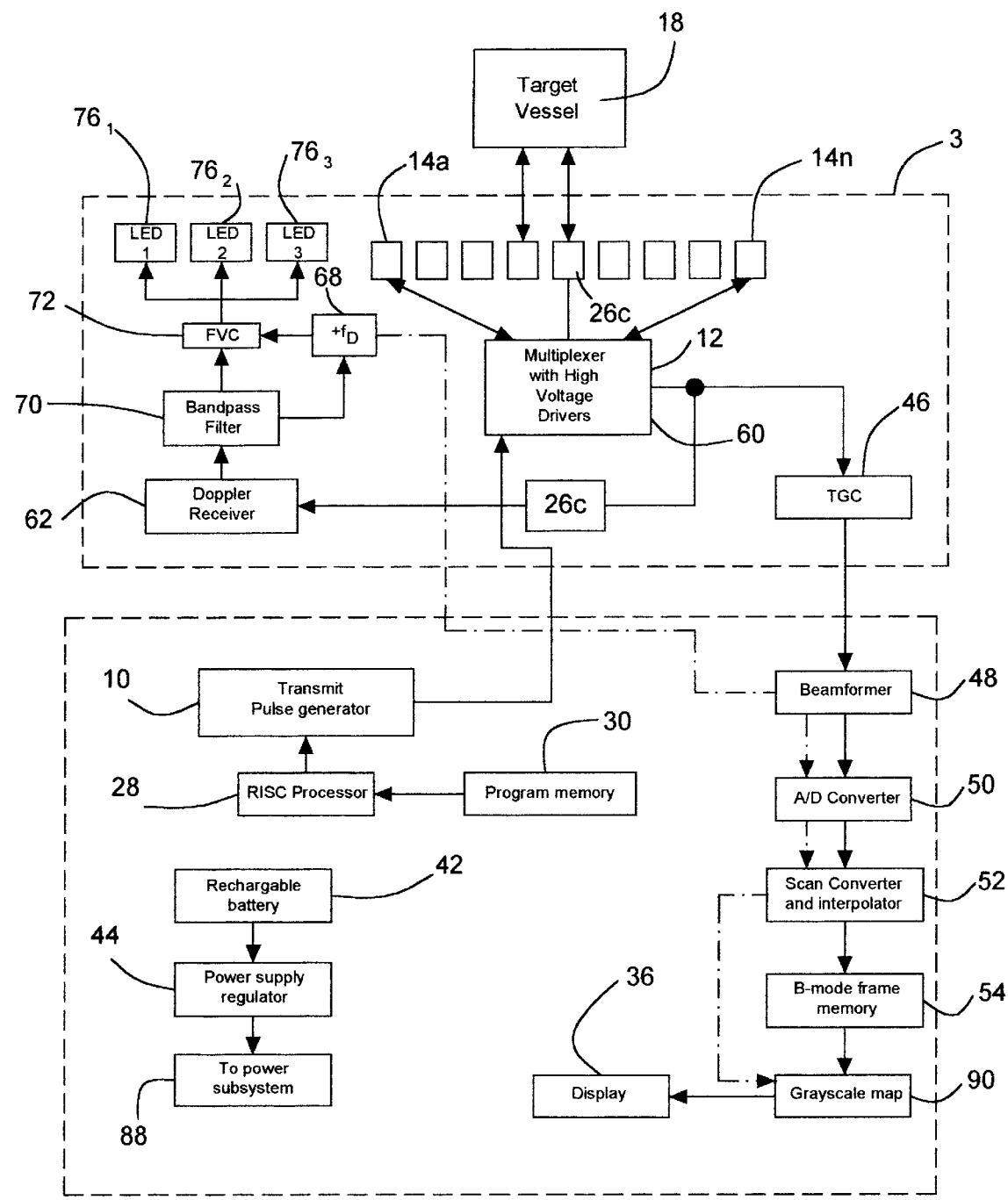
FIG. 2 is a schematic block diagram of the entire imaging system showing the scanhead and principal functional elements in the main housing.
Figure 3:
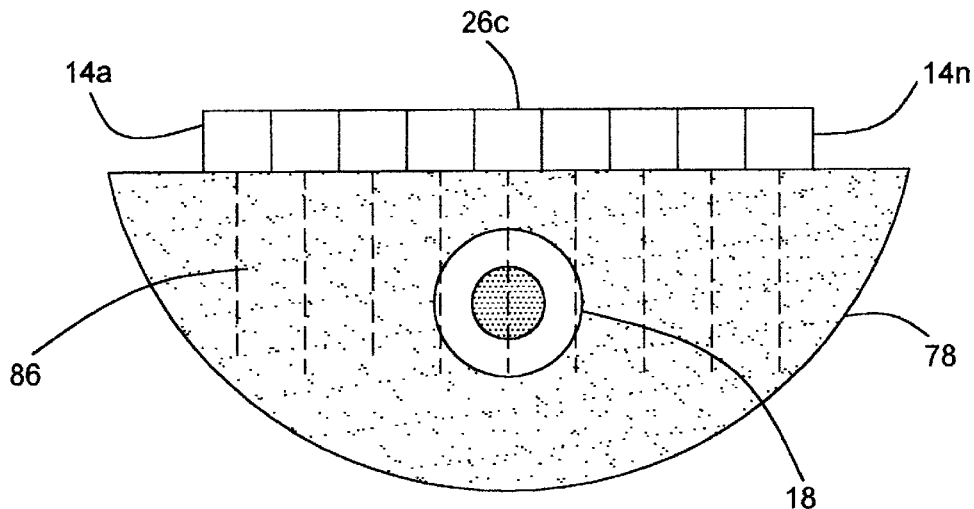
FIG. 3 shows a cross-sectional view of the patient's extremity and the target blood vessel with respect to B-mode scanlines and a separate single doppler scanline.
Figure 4:
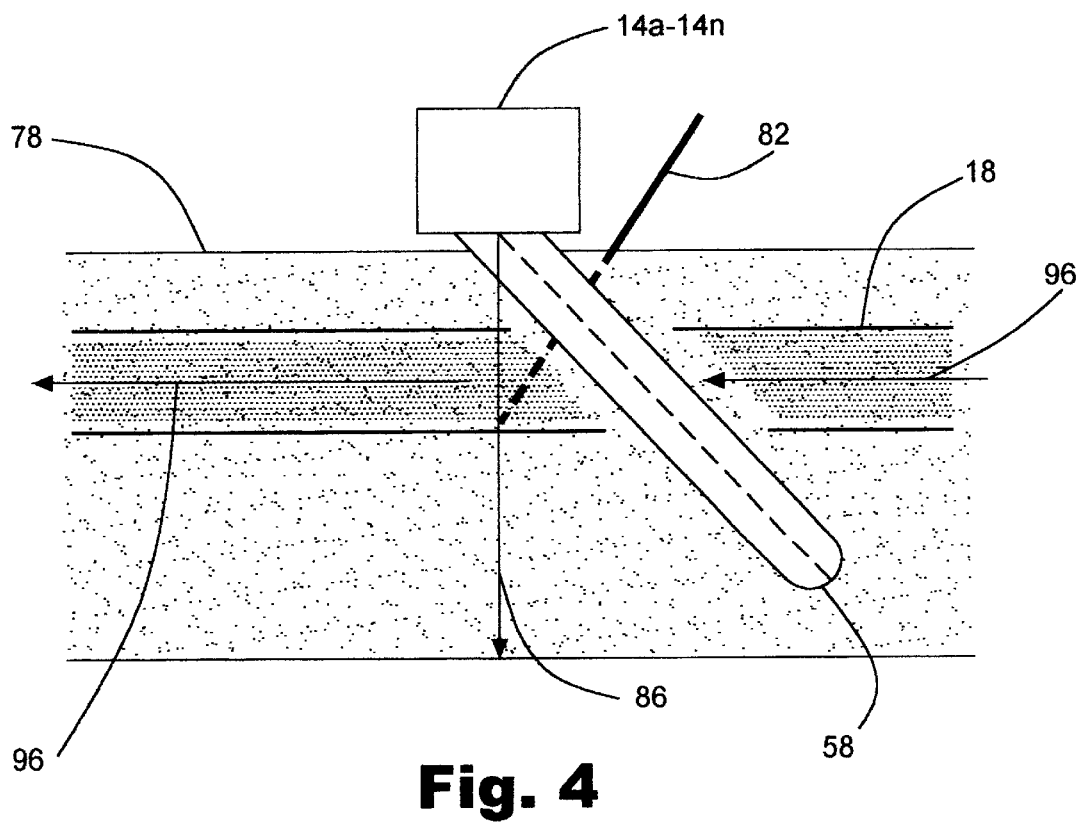
FIG. 4 is an illustration of the doppler angle to detect positive doppler shifts in relation to be perpendicular B-scan acoustic beam and the needle pathway to the target vessel.

As shown in FIG. 2 the entire imaging system is of conventional type which employs a B-mode scan for anatomical imaging of the target blood vessel 18 relative to varying return echo intensities from the area of interest FIG. 3. The system only requires a relatively small transducer aperture requiring use of a fewer transducer elements due to the small scanning area and its intended use for locating peripheral vessels for intravenous cannulation. The varying echo intensities are fed to the time gain compensation (TGC) 46 circuitry for amplification and attenuation compensation, the signal is then transmitted to the beamformer 48, which performs delay and sum functions to form a focused beam. Beamformer functions can also be integrated on a single chip. Data sampling, variable delay and sum and other beamforming functions can be optimized and are well-known to a person skilled in the art and therefore, will not be described in depth for simplicity. The signal information is first digitized by an A/D converter 50 to format suitable scan conversion 52 for subsequent display. It has been pointed out however, that if a digital beam former is implemented, the beamformer output may be fed to the scan converter. The digitized data is sent to the digital scan converter 52 wear a conventional scanline interpolation algorithm is implemented. The interpolated scanline goes through scan conversion process where it's natural polar coordinates are converted to a rectangular or X-Y coordinates utilizing a trigonometric function as follows:

$X = r \cos \theta$ $Y = r \sin \theta$

After conversion to rectangular coordinates has been achieved, the scanline is then stored in a memory chip, B-mode frame memory 54, for subsequent display of a cross-sectional image of the target blood vessel in a two-dimensional grayscale image in real time on the LCD display. The grayscale image is formed by encoding the B-mode echo intensities using a first mapping function of the red, green and blue components.

To allow for system simplification, the display screen 36 monitors the vascular cross-section 56, single Doppler scanline 58 within the intravascular diameter and an alphanumeric display of the vessel depth data may be displayed as an alternative embodiment. For further simplification, the system does not require any other graphical screen overlays, and therefore does not employ graphics processor nor does it require any data input system and circuitry for documentation such as patient demographics etc, hence, the input keyboard will not be implemented.

Figure 5:
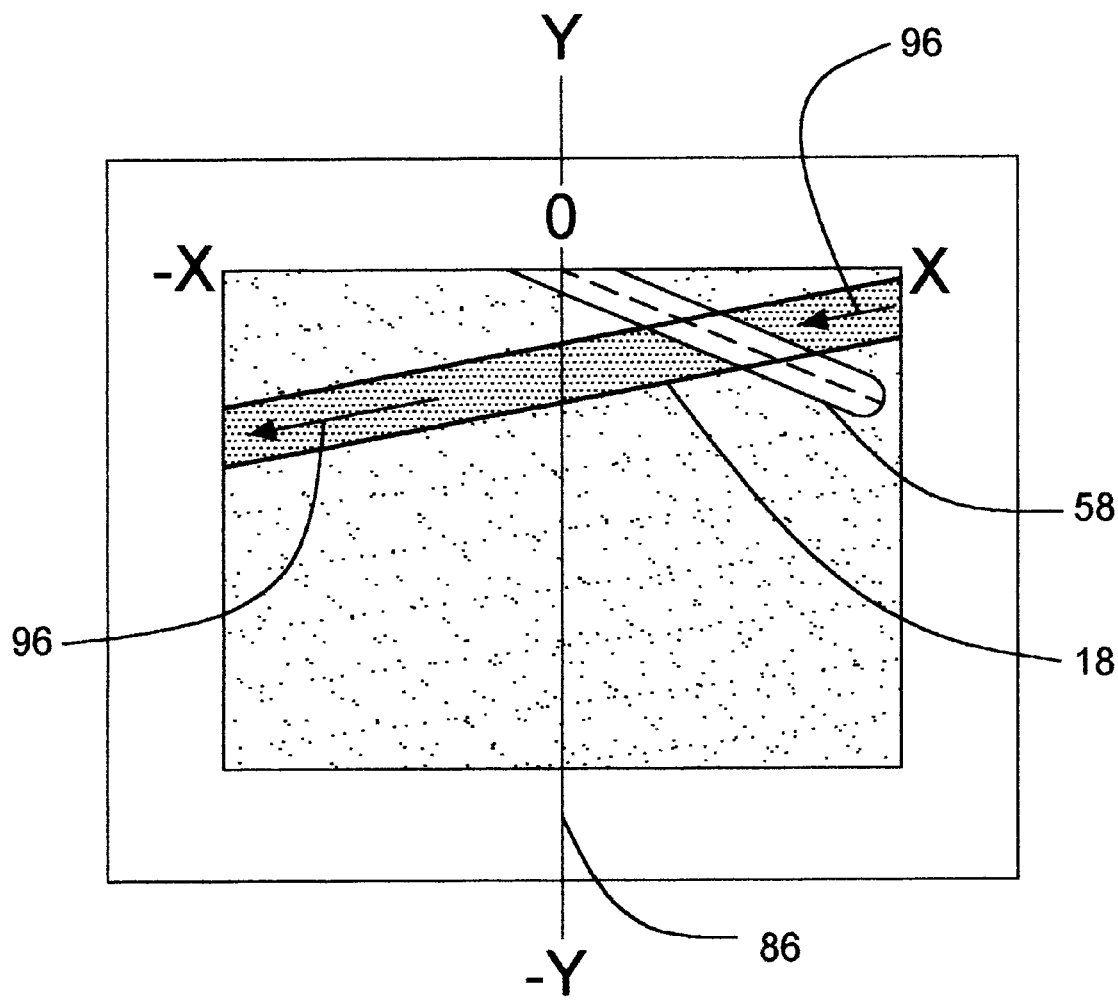
FIG. 5 is a graphical illustration of the doppler angle and the B-scanline in a rectangular cordinate.

In a separate mode, single element transmit the doppler pulses from the pulse generator 10 are supplied only to the center element 26 C., creating a single scanline as it traverses or hits the target blood vessel 18 and functions as a blood vessel sensor to implement another preferred embodiment of the invention. The single element Doppler sensor pulses is preset in a separate mode, controlled by the RISC processor 28 through the transmit multiplexers 12 integrated with a high voltage driver 60. In operation, the center element 26 C is energized with a burst of energy with the predetermined frequency. An example would be a 1 microsecond burst at 7.5 MHz frequency. In another example, the center element 26 C transmits 1 microsecond burst at 50 microsecond intervals for a period of 10 milliseconds, or 200 bursts this center element. This allows detection of Doppler shifts down to 100 Hz. The signal reflected from the moving cell scatterers is received by the same center element 26 C and is processed to detect doppler shift frequency indicating movement of blood cells and various depths underneath the transducer elements. The multiple pulse bursts are applied to the center element 26 C only, which subsequently propagates multiple doppler acoustic beams at a predetermined doppler angle optimized to detect positive doppler shift FIG. 5. The received doppler signal is sent to the doppler receiver 62 as echo voltage, the radio frequency amplifier increases the echo voltage amplitude. The amplifier echo voltage amplitude are mixed in a demodulator 64 with the emitted voltage to yield the sum and difference of the two frequencies then passes through a low pass filter 66 for high frequency rejection to yield the doppler shift frequency 68. The output gets sampled and data held in buffer memory. The output is eventually filtered by a bandpass filter 70 to filter out unwanted signal or noise that did not originate from the reflected doppler signal and to filter out harmonic signals which may be present on the output signal from the demodulator. The output signal from the bandpass filter is converted to a current based output signal by the frequency to voltage converter 72 to drive a plurality of light emitting diode LED 1–3 indicator lights 76 which is described in detail below.

Figure 6:
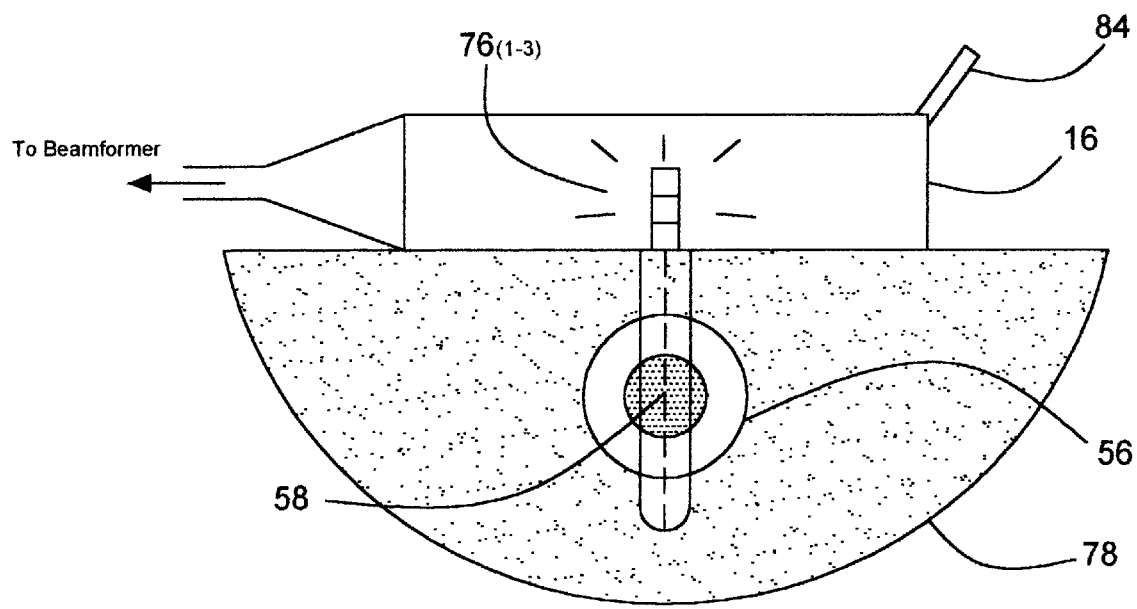
FIG. 6 shows the doppler sensor beam as it traverses the target vessel and the yielded positive doppler shift from the return echo drives the light emitting diode (LED) indicators.
Figure 7:
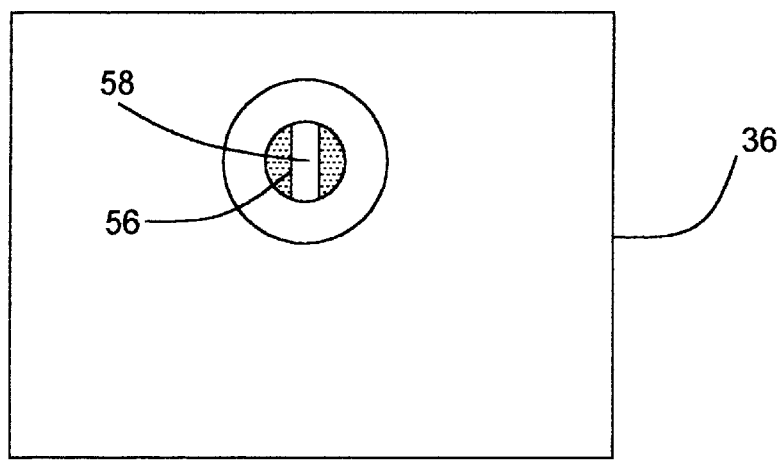
FIG. 7 shows a cross-sectional view of the target vessel as imaged by the B-scan and the single doppler scanline visible within the intravascular diameter serving as a target marker.
Figure 8:
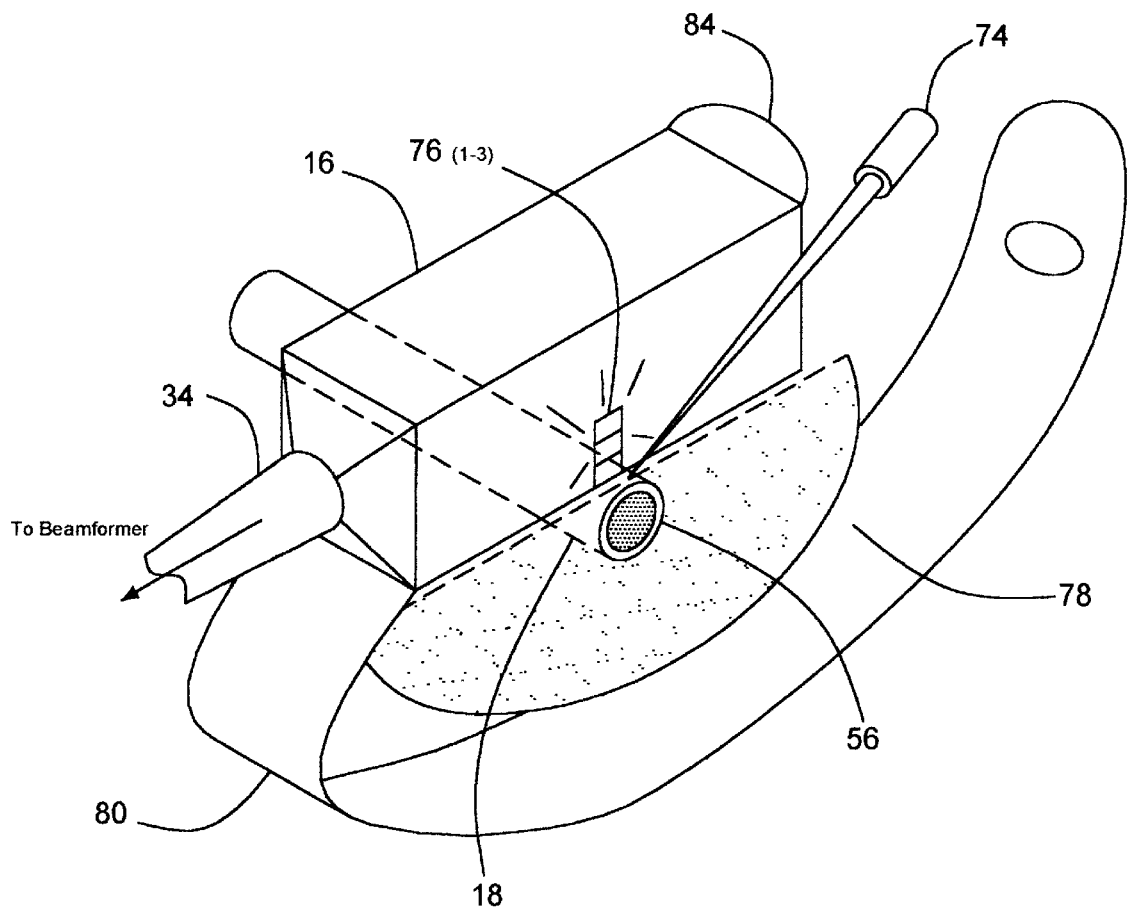
FIG. 8 shows the application of the scanhead on the patients extremity showing the angular position of the needle as it is introduced using the light emitting diode (LED) indicator lights as guide.
Figure 9:
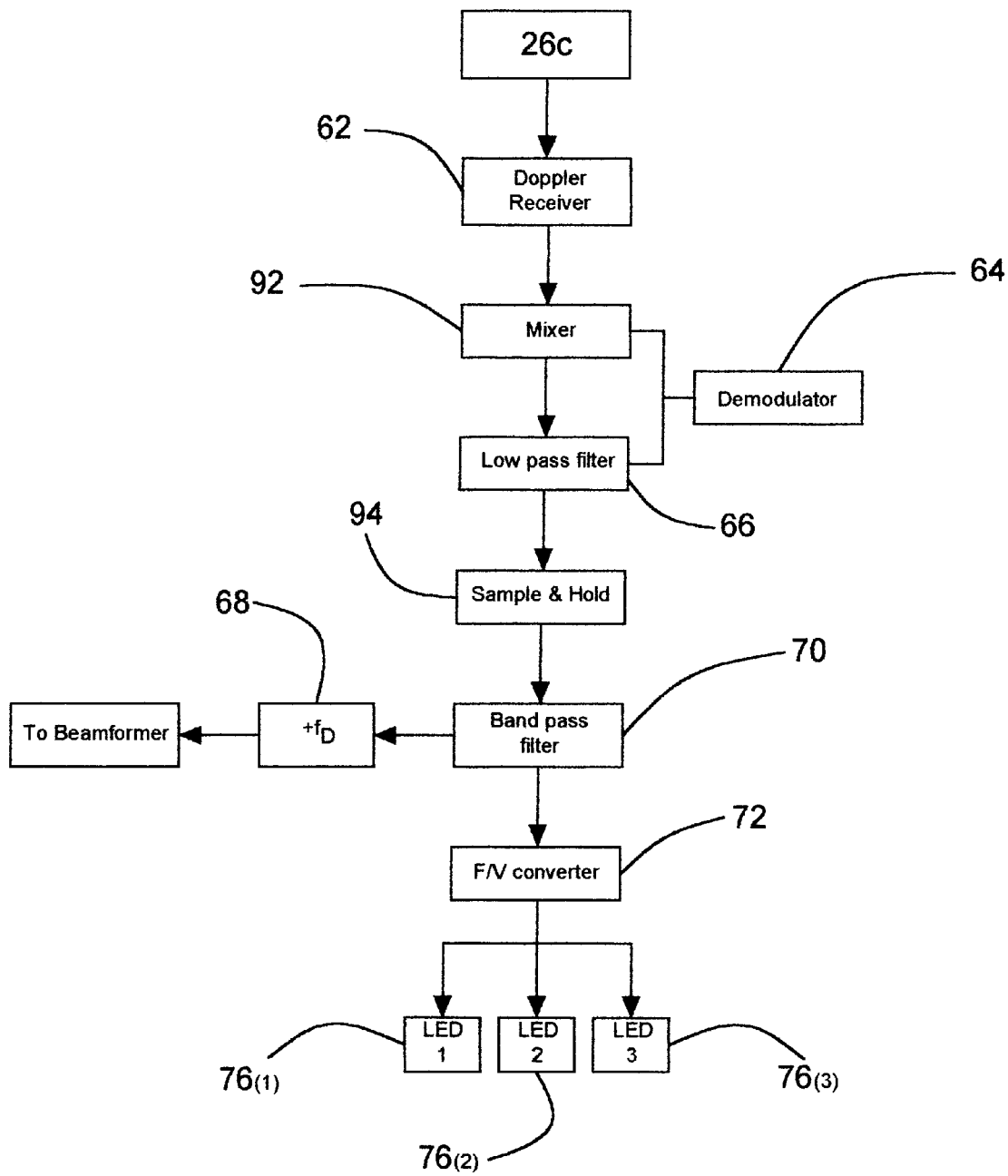
FIG. 9 is a flow diagram of the preferred embodiment of the invention showing the blood vessel sensor by a single doppler scanline to detect positive frequency shifts to subsequently drive the LEDs.

A single scanline produced from multiple doppler pulses which is subsequently displayed superimposed to the B-mode scanned image as it illuminates a portion or all of the vascular cross-section 56. The illumination of the vascular cross-section 56 serves as a marker of the target blood vessel 18, FIG. 7 indicating to the operator that the target blood vessel 18 is underneath and perpendicular to center element. Simultaneously, the same positive doppler frequency shift output from the bandpass filter 70 is converted to an electrical voltage by a frequency to voltage converter 72 that drives and illuminates LED 1–3, FIG. 9 at increasing voltage requirements which is directly related to the increasing positive frequency shift as the center element 26 C. doppler beams traverses the central diameter of the target blood vessel FIG. 6. The LED indicator lights are mounted in the scanhead housing 16 in a manner wherein LED 1 is at the bottom center of the transducer scanhead closest to the aperture, then LED 2 is mounted superiorly to LED 1, and LED 3 mounted superiorly to LED 2 forming a vertical configuration, similar to an arrow pointing downwards to indicate to the operator that precise spot of catheter needle insertion. LED 3 requires the highest voltage requirement. All LED indicator lights should be mounted proximal and parallel to the center element 26 C. The reason for this mounting configuration is when all of LED indicator lights are illuminated the orientation of the target blood vessel 18, is known which is perpendicular and closest to LED 1. As an alternative embodiment, the vessel depth may be displayed on the screen to guide the operator to appropriately adjust the angular positioning of catheter needle prior to needle introduction FIG. 8. And operator is guided by a visual of the target blood vessel provided by that B-scanned image, illuminated partially or 40 by a single doppler scanline 58 traversing the vascular cross-section 56, and the illumination of a plurality of light emitting diode LED 1–3 indicator lights 76 to indicate that precise spot in the patient's extremity 78 where the needle should be inserted related to the target vessel's location and orientation. After the target vessel 18 is located a rubber strap 80 may be adapted to the patient or wrapped around patient's arm by attaching one end to a thin flat curved rubber strap hook mounted on the scanhead FIG. 8. This allows for a hands-free single user operation. The needle is then inserted through the patient's skin successfully to the target blood vessel 18 on a needle pathway 82 guided by the features off the preferred embodiment of the invention. This procedure can be easily perform by both medical and paramedical professionals in a very short period of time allowing rapid and accurate the intravenous cannulation.

CONCLUSIONS, RAMIFICATIONS, AND SCOPE

Accordingly, it can be seen by the intended users both medical in paramedical professionals that the invention provides a user-friendly, fast, safe and accurate way of performing intravenous cannulation procedures on any patient by locating the target blood vessel by real-time ultrasonic B-scan imaging of a target blood vessel, single element doppler scanline vessel sensor and LED indicator lights that guides the operator on the exact spot of needle insertion into the skin, guides the needle to the target vessel in real-time, provides on-screen vessel depth data from the vessel's distance to the transducer elements, and confirms cannula placement status post insertion by simple manipulation of the scanhead.

Although the description above contains to many specificities, these should not be construed as limiting the scope of of the invention but as merely providing illustrations of some of the presently preferred embodiments of this invention. Various other embodiments and ramifications are possible within its scope. For example, it can be manipulated to view a longitudinal segment of the vein to be used to check and confirm infiltration of already established IVs by directly imaging the needle placement status, it can be used as guide for arterial blood draws for arterial blood gas determination. If the scanhead is applied in another superficial area of the body, it can aid in quickly assessing presence of foreign bodies in superficial areas of the skin. With a special curved coupling gel cylinder as a separate attachment to transducer aperture, can be used as a guide in intubating a patient with endotracheal tube as an emergency procedure by imaging the cross-section of the trachea which is anatomically superficial. If used with a transducer with a lower operating frequency e.g. 2 MHz, it can possibly guide a central venous catheter needle being inserted in either side off the superior vena cava etc.

Thus, the scope of the invention should be determinined by the appended claims and their legal equivalents, rather than by the examples given.

We claim:

1. A dual mode handheld ultrasonic device for guiding an intravenous catheter into a target blood vessel comprising:
    an array transducer scanhead;
    a B-mode image processor with a predetermined operating frequency means for locating and imaging a cross section of said target blood vessel;
    a single element doppler mode means for detecting said target blood vessel to create a single doppler beam marker image superimposed to said cross-sectional image;
    means for indicating a precise catheter insertion site on a patient's extremity;
    wherein said transducer, said B-mode processor and said single element doppler processor are located in two or more separate enclosures.

2. The handheld ultrasonic device of claim 1, wherein said array transducer is flat linear array with a predetermined aperture.

3. The handheld ultrasonic device of claim 1, wherein said array transducer is located in a scanhead housing with a predetermined size.

4. The array transducer scanhead of claim 1, further comprising:
    a multiplexer fabricated in an integrated circuit for sequentially pulsing the elements in the array;
    a doppler receiver for demodulating received doppler signals;
    a bandpass filter for filtering said doppler signals;
    a frequency to voltage converter for converting said filtered doppler signals to variable electrical voltages;
    a plurality of light emitting diode indicator lights for indicating a precise catheter insertion site on a patient's extremity with respect to the location of the target blood vessel;
    a time gain compensation function for receiving returning echo frequencies from the target blood vessel and relaying said frequencies to the beamformer.

5. The array transducer scanhead of claim 1 further comprising means for securing said scanhead housing with a rubber strap adapted to the patient's extremity after the target blood vessel has been located to allow for a hands free single user operation.

6. The flat linear array transducer of claim 2 is disposed in said scanhead housing in close proximity to the patient's skin and said light emitting diode indicator lights.

7. The single element doppler processor of claim 1, wherein a series of doppler beams are transmitted and received through the center element of the array at a different angle from said B-mode acoustic beams for maximum detection of positive doppler shifts as it senses the blood flow within the target blood vessel.

8. The light emitting diode LED indicator lights of claim 4 are activated by said positive doppler shifts detected by said single element doppler beam as it hits the target blood vessel.

9. A main image processing housing coupled to the array transducer scanhead by a coiled cable comprising:
    a beamformer wherein the beamforming function is fabricated on an integrated circuit;
    a pulse generator fabricated on an integrated circuit for generating and sequencing of ultrasonic pulses;
    a scan converter fabricated on an integrated circuit for converting display coordinates;
    a rechargeable battery and power supply regulator for variable voltage requirements of the imaging system;
    a display screen;
    a plurality of adjustment knobs on the exterior of said main image processing housing.

* * * * *